(12) United States Patent
Shrivastava

(10) Patent No.: US 7,828,916 B2
(45) Date of Patent: Nov. 9, 2010

(54) METHODS OF CRIMPING EXPANDABLE MEDICAL DEVICES

(75) Inventor: Sanjay Shrivastava, Mountain View, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 614 days.

(21) Appl. No.: 11/781,180

(22) Filed: Jul. 20, 2007

(65) Prior Publication Data

US 2008/0021543 A1 Jan. 24, 2008

Related U.S. Application Data

(60) Provisional application No. 60/807,870, filed on Jul. 20, 2006.

(51) Int. Cl.
*C22F 1/10* (2006.01)

(52) U.S. Cl. .................................. 148/563; 148/676

(58) Field of Classification Search .................. 148/561
See application file for complete search history.

(56) References Cited

U.S. PATENT DOCUMENTS

| 6,503,272 | B2 * | 1/2003 | Duerig et al. .............. 623/1.24 |
| 6,629,350 | B2 | 10/2003 | Motsenbocker | |
| 6,915,560 | B2 | 7/2005 | Austin | |
| 2005/0154450 | A1 | 7/2005 | Larson et al. | |
| 2005/0182475 | A1 | 8/2005 | Jen et al. | |
| 2007/0079494 | A1 | 4/2007 | Serrano | |

* cited by examiner

*Primary Examiner*—George Wyszomierski
(74) *Attorney, Agent, or Firm*—Jonathan Feuchtwang; Squire, Sanders & Dempsey, L.L.P.

(57) ABSTRACT

Disclosed are methods for crimping a medical device, such as a stent, wherein the medical device is formed of a superelastic alloy. A method for crimping a medical device includes cooling the stent until the alloy becomes martensitic, allowing the stent to warm after cooling, crimping the stent with a crimping apparatus.

18 Claims, 4 Drawing Sheets

METHODS OF CRIMPING EXPANDABLE MEDICAL DEVICES

This application claims the benefit of U.S. Provisional Application No. 60/807,870, filed Jul. 20, 2006.

BACKGROUND OF THE INVENTION

1. Field of the Invention

This invention relates generally to methods for crimping expandable medical devices, more particularly, to methods and processes for crimping medical devices constructed of superelastic alloys.

2. Description of the State of the Art

Materials, organic and metallic, are capable of possessing shape memory. A device made of such materials can be deformed from an original, heat stable configuration to a second, heat-unstable configuration. The device is said to have shape memory for the reason that, upon the application of heat alone, it reverts, or to attempts to revert, from its heat-unstable configuration to its original, heat stable configuration. That is, the device "remembers" its original configuration with the application of heat.

Among metallic alloys, the ability to possess shape memory is a result of the alloy undergoing a reversible transformation from an austenite molecular structure to a martensite molecular structure with a change in temperature. An alloy having an austenite or martensite molecular structure are generally described as austenitic or martensitic, respectively. Alloys capable of this transformation are known generally as shape memory alloys (SMAs). This transformation is sometimes referred to as a thermoeleastic martensitic transformation. An article made from an SMA, a hollow sleeve, for example, is easily deformed from its original configuration to a new configuration when cooled below the temperature at which the alloy is transformed from the austenitic state to the martensitic state. The temperature at which this transformation to the martensitic state starts is referred to as Ms and the temperature at which it finishes is referred to as Mf. That is, the transformation to the martensitic state occurs over a temperature range of Ms to Mf. When the article is deformed and later warmed to the temperature at which the alloy starts to revert to the austenitic state, referred to as As, austenite structures begin to form in the alloy and are interdispersed among martensite structures. At about this stage, the deformed article will begin to return to its original, undeformed configuration. The temperature at which the alloy reverts completely to the austenite state is referred to as Af.

Many shape memory alloys (SMAs) are known to exhibit stress-induced martensite (SIM). When an SMA sample exhibiting stress-induced martensite is stressed at a temperature above Ms (so that the austenitic state is initially stable), but below Af (the maximum temperature at which martensite formation can occur even under stress) it first deforms elastically and then, at a critical stress, begins to transform by the formation of stress-induced martensite. The behavior of the SMA sample when the deforming stress is released differs depending on whether the temperature of the SMA sample is above or below As. If the temperature is below As, the stress-induced martensite is stable; but if the temperature is above As, the martensite is unstable and transforms back to austenite, with the SMA sample returning (or attempting to return) to its original shape. This temperature-dependant behavior when stress is released, along with the shape memory effect, is seen in almost all alloys which exhibit a thermoelastic martensitic transformation. However, the extent of the temperature range over which the SIM is seen and the stress and strain ranges associated with the above-described temperature-dependant behavior vary greatly among SMAs.

SMAs are commonly utilized in the medical field. For example, U.S. Pat. No. 3,620,212 to Fannon et al. proposes the use of an SMA intrauterine contraceptive device; U.S. Pat. No. 3,786,806 to Johnson et al. proposes the use of an SMA bone implant; and U.S. Pat. No. 3,890,977 to Wilson proposes the use of an SMA element to bend a catheter or cannula.

A more common application for SMAs are medical devices such as stents, which can be relatively small and intricate. For example, U.S. Pat. No. 7,128,756, entitled "Endoprosthesis Having Foot Extensions," the entirety of which is hereby incorporated by reference, illustrates exemplary embodiments of stents which may be formed of an SMA such as Nitinol.

These medical SMA devices rely on the property of shape memory to achieve their desired clinical effect. That is to say, they rely on the characteristic, that when an SMA element of the device is cooled while in its original shape and size to its martensitic state and is subsequently deformed, it will retain its deformed shape and size; and when it is warmed to its austenitic state, the original shape and size will be recovered.

Stents formed of an SMA are generally heat set to an expanded diameter. Thus, to facilitate delivery within a vessel or artery, they must be crimped to and retained at a smaller diameter. The stents are usually crimped utilizing a stent crimping apparatus such as shown and described in U.S. Pat. No. 6,629,350. The crimped stent is then placed into a delivery device. U.S. patent application Ser. No. 10/932,964, entitled "Delivery System for a Medical Device," the entirety of which is herein incorporated by reference, shows an exemplary stent delivery system, wherein a stent is disposed within a receiving area at the distal end of the delivery system and a slidable sheath covers the stent. To deliver the stent, the delivery system is tracked over a guidewire to a desired location wherein the slideable sheath is retracted from the covering the stent, thereby allowing the stent to expand from its crimped diameter to its expanded diameter.

However, the use of the shape memory effect in the field of stents has a disadvantage in that it is difficult to crimp the stent at or near room temperature and load it into a delivery device without damaging the stent or the delivery device. Additionally, at or near room temperature, the stent is very bendable and flexible, and may have high hoop strength.

Therefore, there is a need for a process for crimping and loading stents made of SMA that allows for easy loading and reduces the risk of damaging the stents or the delivery system during the crimping/loading process. There is also a need for a method of crimping a stent constructed of an SMA that takes advantage of its shape memory property, i.e., its ability to return to an original shape after relatively substantial deformation, without hindering the crimping or loading process. The present invention satisfies these and other needs.

SUMMARY OF THE INVENTION

Briefly and in general terms, the present invention is directed to methods for crimping medical devices such as stents.

In aspects of the present invention, a method of crimping a medical device comprises selecting a medical device fabricated at least partially from an alloy having shape memory properties, wherein the medical device has an expanded diameter, cooling the device to a temperature below an Ms temperature of the alloy to form thermally induced martensite, heating the device to a temperature between an Mf temperature and an As temperature of the alloy, disposing the device within an aperture of a crimping apparatus, and activating the crimping apparatus such that the device, while disposed within the aperture, is reduced from the expanded diameter to a crimped diameter, the crimped diameter less than the expanded diameter, wherein the temperature of the device is maintained between the Mf and the As temperatures during crimping such that the thermally induced martensite is maintained in the alloy.

In other aspects of the present invention, a method of crimping an implantable device comprises obtaining an implantable device comprising an alloy, the device having a first size when the alloy is austenitic, allowing the device to cool from a first temperature, at which the alloy is austenitic, to a second temperature such that the alloy becomes martensitic, allowing the device to warm from the second temperature to a third temperature while the alloy remains martensitic, and deforming the device while the alloy remains martensitic such that the device has a second size smaller than the first size.

In yet other aspects of the present invention, a method of crimping a medical device comprises obtaining a device comprising an alloy, the device having a first size when the alloy is mostly or entirely austenite, causing thermally induced martensite to form in the alloy, allowing the stent with thermally induced martensite formed in the alloy to warm to a selected temperature above an Ms temperature of the alloy, and deforming the device at the selected temperature such that the device has a second size less than the first size.

The features and advantages of the invention will be more readily understood from the following detailed description which should be read in conjunction with the accompanying drawings.

DETAILED DESCRIPTION OF THE PREFERRED EMBODIMENTS

The following detailed description should be read with reference to the drawings in which similar elements in different drawings are numbered the same. The drawings, which are not necessarily to scale, depict illustrative embodiments and are not intended to limit the scope of the invention.

In accordance with the present invention, there are provided methods of crimping a medical device constructed of a shape memory alloy (SMA). Exemplary embodiments of medical devices which may be processed according to the methods of the present invention include, without limitation, stents, filters, coils, and other implantable medical devices which have a delivery diameter and a deployed diameter greater than the delivery diameter. Generally, in accordance with the methods of the present invention, the term stent will be utilized to described a generally tubular implantable medical device. In a preferred embodiment, a stent is constructed of a shape memory alloy, such as Nitinol.

Figure 1:
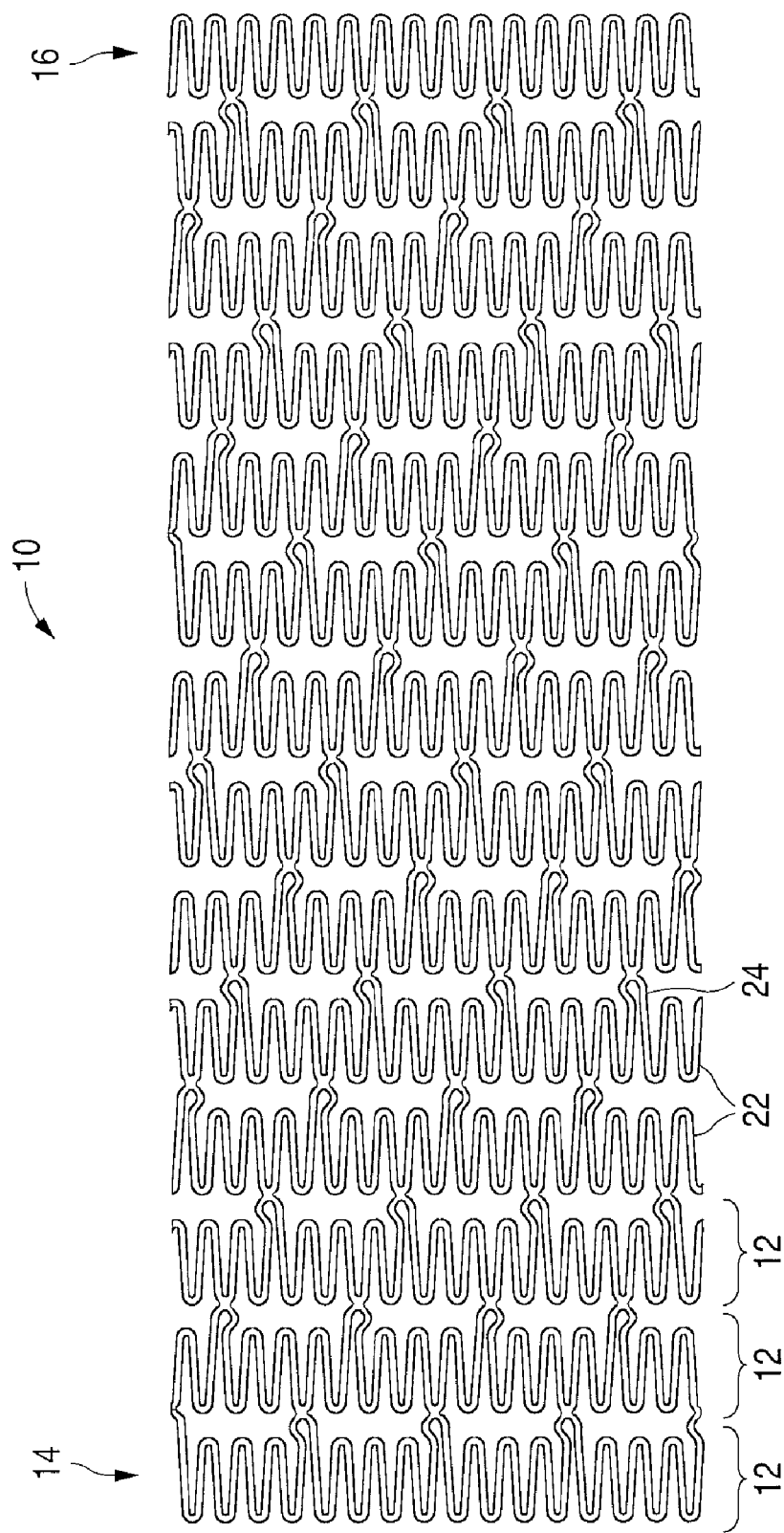
FIG. 1 is a plan view of a stent showing a flattened pattern of undulating rings and interconnecting members.
Figure 2:
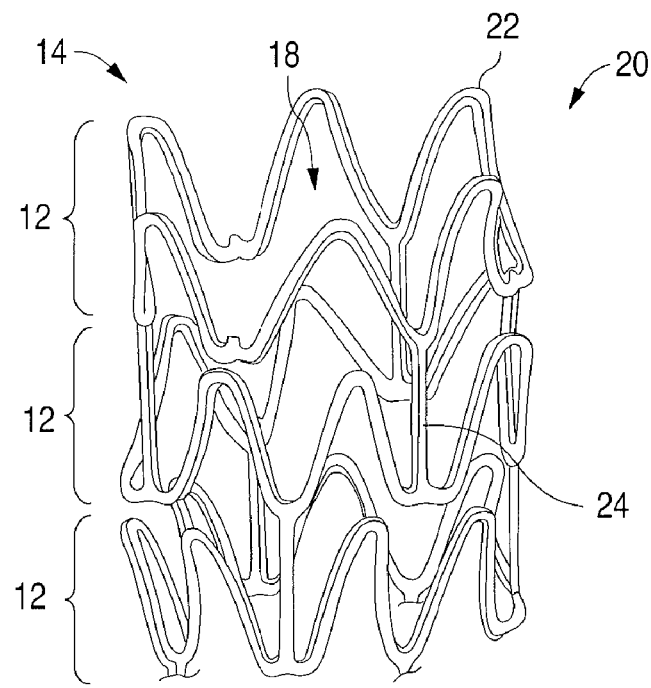
FIG. 2 is perspective view of a first end region of a stent showing undulating rings and interconnecting members defining a generally tubular member having a lumen.

Referring now in more detail to the exemplary drawings for purposes of illustrating embodiments of the invention, wherein like reference numerals designate corresponding or like elements among the several views, there are shown in FIGS. 1 and 2 stents 10, 20 comprising a plurality of rings 12 forming an elongated tubular member having a first end 14, a second end 16, and a lumen 18 extending therethrough. The stents 10, 20 generally have an expanded diameter established by a series of expansion and heat-treating processes. The rings 12 form a pattern of undulating elements 22 and interconnecting elements 24. The pattern may be cut in the wall of the tubular member by a laser. After the pattern has been cut, the tubular member is placed through a series of processes to expand its diameter to a desired final diameter. The tubular member is heat treated to set the final diameter of the stent and to establish the superelastic properties of the stent.

Figure 3:
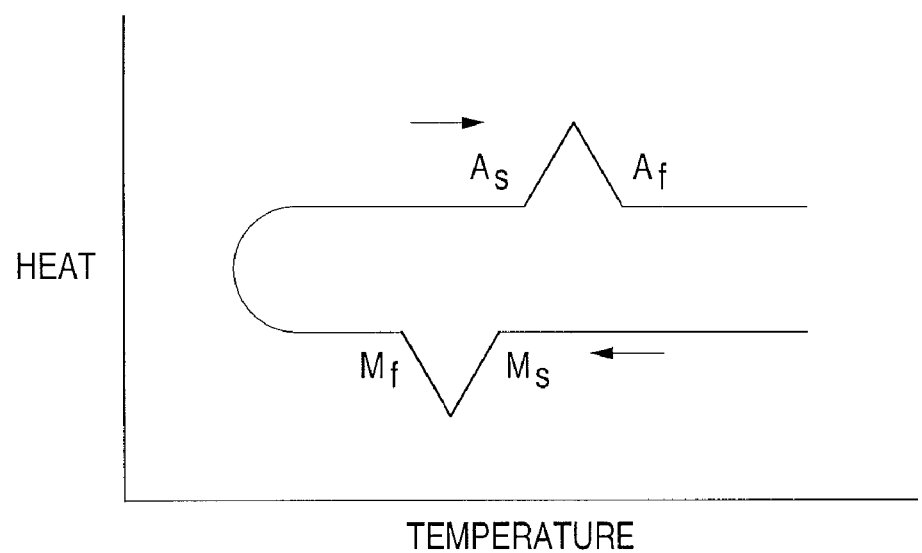
FIG. 3 is an exemplary phase diagram for a Nitinol material of which a stent may be fabricated.

In FIG. 3, a phase diagram of an SMA, such as Nitinol, illustrates the phase change of the SMA as a function of temperature and heat, wherein the SMA undergoes an elemental phase change from martensitic to austenitic depending upon temperature and heat. Different compositions of Nitinol exist. Nitinol having a composition of 50.4 atomic % nickel and 49.5 atomic % titanium may have an As temperature of about 10 degrees C., an Af temperature of about 20 degrees C., an Ms temperature of about −40 degrees C., and an Mf temperature of about −60 degrees C. As the temperature is decreased from room temperature, the stent initially in an austenitic phase begins to transition to the martensitic phase. During this transition, the mechanical properties of the stent change as well. The stent transforms from (a) elastically deforming and being able to recover from applied forces to (b) plastically deforming in response to applied forces.

In accordance with the present invention, there are provided methods for crimping a stent formed of Nitinol from a heat-set, expanded diameter to a delivery diameter for loading within a delivery system. The disclosed methods improve the ability to load the crimped stent into a delivery system while minimizing potential damage to the stent during the loading process.

In accordance with an exemplary embodiment of the present invention, the method comprises the following steps. Fabricating a stent of Nitinol such that the stent has an expanded, heat-set, final diameter. Cooling the stent from a first temperature to a second temperature less than the first temperature such that Nitinol undergoes a complete phase transformation to martensite. Heating the stent from the second temperature to a third temperature below As. Placing the stent in a crimping device. Reducing the diameter of the stent from the heat-set, final diameter to a crimped diameter. Disposing the crimped stent into a delivery system.

Figure 4:
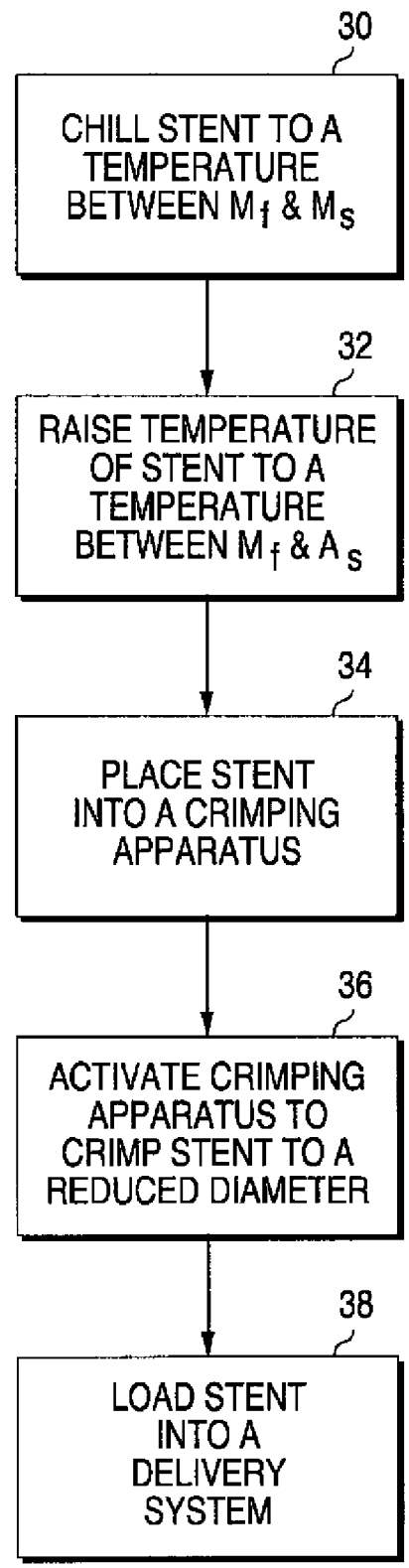
FIG. 4 is functional flow diagram showing a method of crimping a stent.

In FIG. 4, a functional flow chart illustrates a crimping method.

At box 30, a stent having an expanded diameter and having been manufactured of a selected material having superelastic properties, such as Nitinol, is cooled to a temperature between Ms and Mf of the selected material.

At box 32, the stent is raised to a temperature between Mf and As, wherein the molecular structure of the selected material is retained in a complete martensitic state.

At box 34, the stent is placed into a crimping apparatus. An exemplary crimping apparatus, as shown in U.S. Pat. No. 6,629,350, comprises a plurality of blades defining an aperture therethrough, the blades being movable to enlarge or reduce the diameter of the aperture.

At box 36, blades of the crimping apparatus are moved thereby reducing the diameter of the aperture and the stent contained therein. The stent is reduced from an expanded heat-set diameter to a diameter small enough to enable the stent to be placed within a delivery system. It is further contemplated that the blades of the crimping apparatus may be cooled or treated to control the temperature of the stent during the crimping process. A stream of chilled or heated air may be forced through the aperture of the crimper at any time during the crimping process.

At Box 38, the crimped stent is loaded into a delivery system such as shown in co-pending U.S. patent application Ser. No. 10/932,964, entitled "Delivery System for a Medical Device," the entirety of which is hereby incorporated by reference. Typically the stent is disposed over a tubular member defining a guidewire lumen and a second tubular member is disposed around the stent. As the temperature of the stent is increased due to removal of the cooling device, the SMA of which the stent is formed may undergo a phase transformation from the martensitic phase to a thermally induced austenitic phase depending on the material properties of the SMA.

In accordance with the present invention, it is contemplated that the method described above may be modified by omitting the step at box 32, wherein the stent, after having been chilled to a temperature between Ms and Mf, is placed directly into the apparatus of the crimper and crimped according to the method described above.

Figure 5:
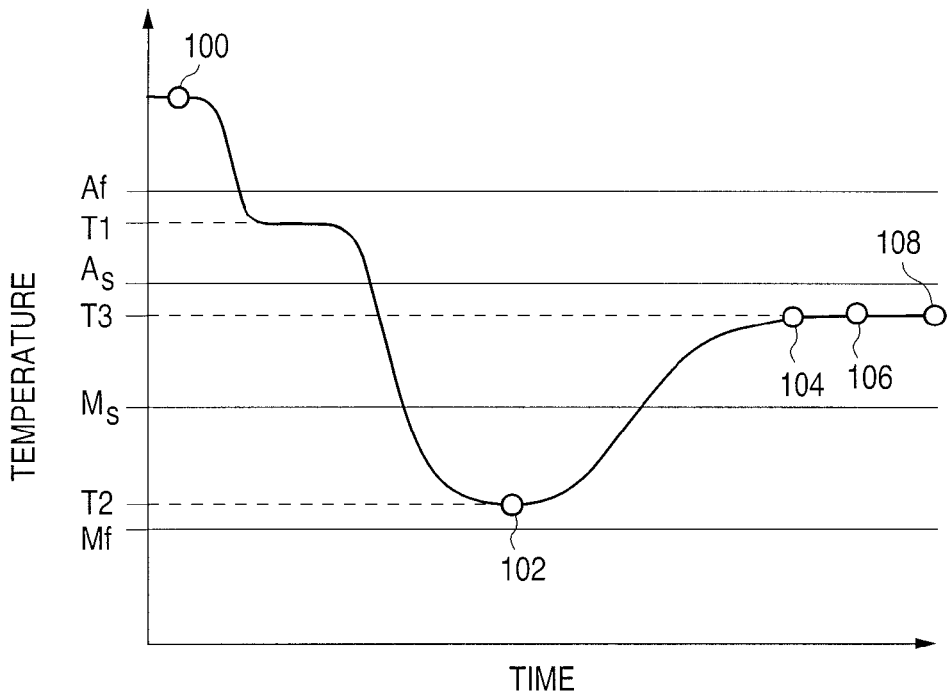
FIG. 5 is a temperature-time chart showing another method of crimping a stent.

Referring now to FIG. 5, a temperature-time chart illustrates a method in accordance with the present invention. First, an implantable device is obtained. The device comprises an alloy exhibiting shape memory behavior. The alloy exhibits an austenitic-to-martensitic phase change starting at an Ms temperature and finishing at an Mf temperature below the Ms temperature. The alloy exhibits a martensitic-to-austenitic phase change starting at an As temperature and finishing at an Af temperature above the As temperature.

In the illustrated embodiment of FIG. 5, the As temperature is above the Mf temperature. In other embodiments, the As temperature is below the Mf temperature.

In addition to metal composition, heat treating parameters, such as temperature and dwell time, may affect the Af, As, Ms, and Mf temperatures of a particular SMA sample. For example, an SMA sample may have Af within about 10 degrees C. to about 35 degrees C., As within about −10 degrees C. to about 25 degrees C., Ms within about −20 degrees C. to about −60 degrees C., and Mf below about −50 degrees C.

At point 100 of the chart, the device has a first size when the alloy is austenitic. At point 102, the device has been allowed to cool from a first temperature, T1, at which the alloy is austenitic, to a second temperature, T2, such that the alloy become martensitic. As used with reference to FIG. 5, austenitic means that a majority or all of the alloy is austenite, and martensitic means that a majority of all of the alloy is martensite. The first temperature T1 can be any temperature above Mf at which the majority of the alloy is austenite. In the illustrated embodiment, the first temperature T1 is between As and Af. The second temperature T2 can be any temperature below Ms at which the majority of the alloy is martensite. In the illustrated embodiment of FIG. 5, the second temperature T2 is between Ms and Mf.

In other embodiments, the second temperature T2 is at or below Mf. When the second temperature T2 is below Mf, thermally induced martensite is formed throughout the entire alloy and the alloy includes no austenite.

With continued reference to FIG. 5, at point 104 the device has been allowed to warm from the second temperature T2 to a third temperature T3 while the alloy remains martensitic. In the illustrated embodiment, the third temperature T3 is between Ms and As. In other embodiments, the third temperature T3 is between As and Af.

At point 106 of the chart, the device is deformed while the alloy remains martensitic such that the device has a second size smaller than the first size.

The device may be a stent or other implantable device. In which case, at point 108 of the chart, the device is loaded into a delivery assembly for delivering the device to a treatment site within a patient. Loading may include placing the device on a catheter and covering the device with a removable sheath to maintain the device in its smaller, second size.

Warming to the third temperature T3 allows for economic and reliable operation of automated crimping equipment. Without the warming step, crimping would be performed at a lower temperature, namely T2, which requires the use of more expensive automated crimping equipment specially designed to operate at low temperatures with reliability and accuracy.

Figure 6:
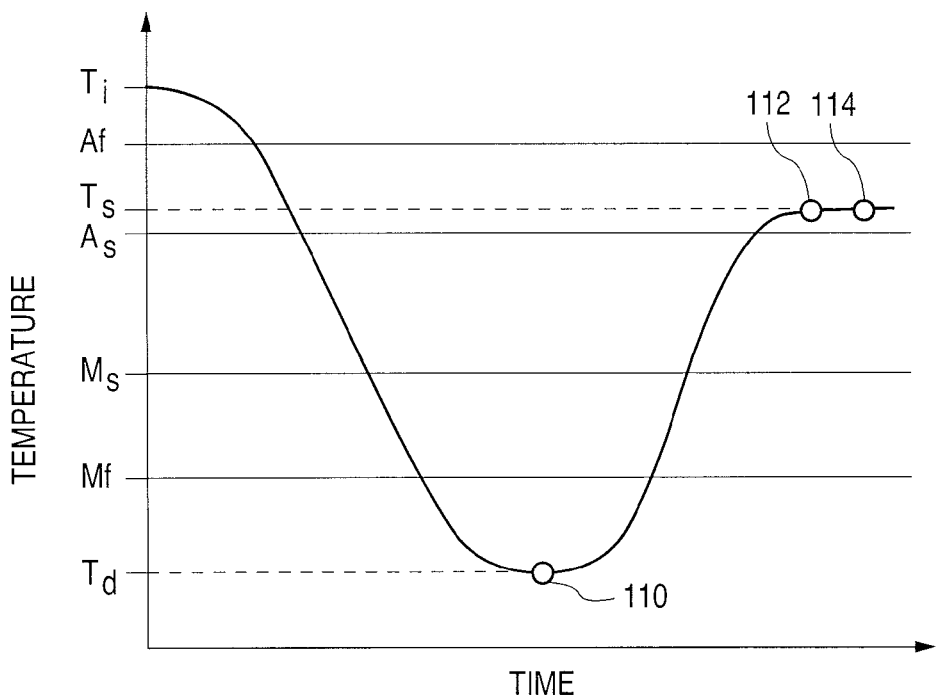
FIG. 6 is a temperature-time chart showing yet another method of crimping a stent.

Referring next to FIG. 6, another temperature-time chart illustrates a method in accordance with the present invention. First, an implantable device is obtained. The device comprises an alloy capable of changing between complete austenite and complete martensite and capable of having interdispersed formations of austenite and martensite. An example of a suitable shape memory alloy includes, without limitation, Nitinol having a selected composition of nickel and titanium and, optionally, having been heat treated such that the As temperature is above the Ms temperature. The device is processed such that it has a first size when the alloy is mostly or entirely austenite.

At point 110, thermally induced martensite has formed in the alloy by cooling the device from an initial temperature, Ti, which is above Af in the illustrated embodiment, to a dwell temperature, Td, below Mf. Because Td is below Mf, thermally induced martensite is formed throughout the entire alloy.

In other embodiments, the initial temperature, Ti, is between Ms and Af. Also, in other embodiments, austenite is allowed to remain with the thermally induced martensite formed in the alloy by cooling the device from Ti to Td that is between Ms and Mf.

With continued reference to FIG. 6, at point 112 the stent has been allowed to warm from the dwell temperature, Td, to a selected temperature, Ts, which is above Ms and below Af. In this way, some of the thermally induced martensite remains in the alloy to facilitate crimping. Preferably, Ts is selected to correspond to an operating temperature of a crimping system. Preferably, a majority of the alloy is martensite at Ts in order to avoid damaging the stent during crimping. In the illustrated embodiment, Ts is between As and Af. Because Ts is between As and Af, some austenite is allowed to form in the alloy after point 100 and become interdispersed with the thermally induced martensite.

In other embodiments, the selected temperature Ts is between Ms and As. In this way, austenite is prevented from forming in the alloy after point 110.

At point 114, the device is deformed at the selected temperature Ts such that the device has a second size less than the first size.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method of crimping an implantable device, the method comprising:
   obtaining an implantable device comprising an alloy, the device having a first size when the alloy is austenitic;
   allowing the device to cool from a first temperature, at which the alloy is austenitic, to a second temperature such that the alloy becomes martensitic;
   allowing the device to warm from the second temperature to a third temperature while the alloy remains martensitic; and
   deforming the device at the third temperature while the alloy remains martensitic such that the device has a second size smaller than the first size, wherein the third temperature is greater than or equal to an Ms temperature of the alloy.

2. The method of claim 1, wherein the second temperature is greater than an Mf temperature of the alloy.

3. The method of claim 1, wherein the second temperature is less than or equal to an Mf temperature of the alloy.

4. The method of claim 1 wherein the device is a stent comprising a tubular member, and the first size and second size correspond to a diameter of the tubular member.

5. A method of crimping an implantable device, the method comprising:
   obtaining an implantable device comprising an alloy, the device having a first size when the alloy is austenitic;
   allowing the device to cool from a first temperature, at which the alloy is austenitic, to a second temperature such that the alloy becomes martensitic;
   allowing the device to warm from the second temperature to a third temperature while the alloy remains martensitic; and
   deforming the device at the third temperature while the alloy remains martensitic such that the device has a second size smaller than the first size, wherein the third temperature is greater than or equal to an As temperature of the alloy.

6. The method of claim 5, wherein the second temperature is greater than an Mf temperature of the alloy.

7. The method of claim 5, wherein the second temperature is less than or equal to an Mf temperature of the alloy.

8. The method of claim 5, wherein the device is a stent comprising a tubular member, and the first size and second size correspond to a diameter of the tubular member.

9. A method of crimping an implantable device, the method comprising:
   obtaining an implantable device comprising an alloy, the device having a first size when the alloy is austenitic;
   allowing the device to cool from a first temperature, at which the alloy is austenitic, to a second temperature such that the alloy becomes martensitic;
   allowing the device to warm from the second temperature to a third temperature while the alloy remains martensitic; and
   deforming the device at the third temperature while the alloy remains martensitic such that the device has a second size smaller than the first size, wherein the alloy has an Ms temperature and an As temperature greater than an Ms temperature, and the third temperature is within from about the Ms temperature to about the As temperature.

10. The method of claim 9, wherein the second temperature is greater than an Mf temperature of the alloy.

11. The method of claim 9, wherein the second temperature is less than or equal to an Mf temperature of the alloy.

12. The method of claim 9, wherein the device is a stent comprising a tubular member, and the first size and second size correspond to a diameter of the tubular member.

13. A method of crimping a medical device, the method comprising:
    obtaining a device comprising an alloy, the device having a first size when the alloy is mostly or entirely austenite;
    causing thermally induced martensite to form in the alloy;
    allowing the device with thermally induced martensite formed in the alloy to warm to a selected temperature above an Ms temperature of the alloy; and
    deforming the device at the selected temperature such that the device has a second size less than the first size.

14. The method of claim 13, further comprising causing thermally induced martensite to form entirely throughout the alloy before allowing the device to warm to the selected temperature.

15. The method of claim 13, further comprising allowing austenite to remain with the thermally induced martensite formed in the alloy immediately before allowing the device to warm to the selected temperature.

16. The method of claim 13, further comprising preventing austenite from forming in the alloy prior to deforming the device.

17. The method of claim 13, further comprising allowing austenite to form in the alloy when allowing the device to warm to the selected temperature, the austenite interdispersed with the thermally induced martensite.

18. The method of claim 13, wherein the device is a stent comprising a tubular member, and the first size and second size correspond to a diameter of the tubular member.

* * * * *